(12) United States Patent
Nelson et al.

(10) Patent No.: US 8,119,668 B2
(45) Date of Patent: Feb. 21, 2012

(54) TREATMENT METHODS EMPLOYING HISTAMINE H₃ RECEPTOR ANTAGONISTS, INCLUDING BETAHISTINE

(76) Inventors: Erik B. Nelson, Cincinnati, OH (US); Floyd R. Sallee, Cincinnati, OH (US)

(*) Notice: Subject to any disclaimer, the term of this patent is extended or adjusted under 35 U.S.C. 154(b) by 597 days.

(21) Appl. No.: 12/158,778

(22) PCT Filed: Dec. 26, 2006

(86) PCT No.: PCT/US2006/049321
§ 371 (c)(1), (2), (4) Date: Jan. 15, 2009

(87) PCT Pub. No.: WO2007/076140
PCT Pub. Date: Jul. 5, 2007

(65) Prior Publication Data
US 2009/0298892 A1    Dec. 3, 2009

Related U.S. Application Data

(60) Provisional application No. 60/753,682, filed on Dec. 23, 2005, provisional application No. 60/846,141, filed on Sep. 21, 2006.

(51) Int. Cl.
*A61K 31/4402* (2006.01)

(52) U.S. Cl. .................................................. 514/357
(58) Field of Classification Search ................... 514/357
See application file for complete search history.

(56) References Cited

U.S. PATENT DOCUMENTS

2006/0019998 A1* 1/2006 Wager et al. ................... 514/364

OTHER PUBLICATIONS

Akhtar et al. Effect of thioperamide on modified forced swimming test-induced oxidative stress in mice. Basic Clinical Pharmacolofy & Toxicology 2005, 97, 218-221.*
Ottaviani Histamine receptors in the central nervous system (CNS): Role in the therapy of equilibrium disorders. Otorinolaringologia, 1995 vol. 45, No. 3 pp. 85-89, abstract.*

* cited by examiner

*Primary Examiner* — Jennifer M Kim
(74) *Attorney, Agent, or Firm* — Dinsmore & Shohl LLP

(57) ABSTRACT

Methods of treating depression, binge eating disorder, narcolepsy, excessive daytime sleepiness, substance use disorders, and Prader Willi syndrome, disorders characterized at least in part by hypocortisolemia and decreased activity of the hypothalamic-pituitary-adrenal (HPA) axis, and disorders related to disturbances in circadian rhythm, comprising the step of administering an effective amount of a histamine type 3 (Bb) receptor antagonist, such as betahistine or its pharmaceutically acceptable salts, or its metabolites to an individual.

9 Claims, No Drawings

TREATMENT METHODS EMPLOYING HISTAMINE $H_3$ RECEPTOR ANTAGONISTS, INCLUDING BETAHISTINE

RELATED APPLICATIONS

This application is a National Stage entry of International Application No. PCT/US06/049321, filed Dec. 26, 2006, and claims priority to U.S. Provisional Application Ser. No. 60/753,682, filed Dec. 23, 2005, and U.S. Provisional Application Ser. No. 60/846,141, filed Sep. 21, 2006.

TECHNICAL FIELD

The present invention relates to the pharmaceutical and medicinal arts and specifically relates to methods of treating diseases and disorders that include symptoms arising from activity and disturbances in activity of the central histamine system, including, for example, methods for treating atypical depression, disturbances in circadian rhythm, and disorders characterized by hypocortisolemia and low hypothalamic-pituitary-adrenal (HPA) axis activity.

BACKGROUND

The brain's histamine system is involved in numerous important regulatory functions that are critical to emotional and physical well-being, including contributing to the control of mood, cognitive functioning (including memory and attention processes), arousal and sleep patterns (including diurnal and seasonal variation), appetite, neuroendocrine responses to stress and other stimuli, and brain reward processing systems. Histamine is a neurotransmitter in the central nervous system that is involved in the regulation of sleep, appetite, cognition, and, perhaps, mood. Agents such as the first generation antihistamines that block histamine type 1 ($H_1$) receptors in the brain are known to cause sedation and increased appetite/weight gain.

Certain subtypes of depression have been associated with decreased function of the hypothalamic-pituitary-adrenal (HPA) axis as evidenced by low cortisol and/or decreased CRH and ACTH levels. Histamine has been shown to enhance the secretion of ACTH and cortisol. In addition, histamine has been shown to increase the synthesis of corticotropin releasing hormone (CRH) mRNA in rat hypothalamus. Conversely, blocking the $H_1$ receptor has been shown to diminish the ACTH response to stress (Knigge, Willems et al. 1999). Studies performed by the present inventors and colleagues have also shown that in rats betahistine increases the cortisol response to stress, and counteracts the decrease in cortisol observed after dexamethasone administration. Moreover, a recent study reported that the MAOI antidepressant phenelzine also increases cortisol levels in mice (Kier et al., 2005), which is relevant to the treatment of atypical depression as MAOIs are superior to other antidepressants classes such as tricyclic antidepressants, which have been reported to decrease cortisol secretion. In summary, both the H3 antagonist betahistine and MAOIs, which are the most proven antidepressants in atypical depression (i.e. hypocortisolemic depression), exhibit the property of increasing HPA axis activity in animal models.

MAOI antidepressants have been shown to decrease the metabolism of histamine, and thereby may increase histamine levels in the brain. Conversely, TCAs, which are less effective than MAOIs in atypical depression have significant antihistaminic activity. Moreover, histamine enhancing compounds, particularly $H_3$ receptor antagonists, have been reported to inhibit monoamine oxidase activity in animal studies.

Evidence suggests that tricyclic antidepressants (TCAs) and possibly serotonin reuptake inhibitors (SRIs) have decreased efficacy in treating atypical depression as these agents have been reported to be less effective than monoamine oxidase inhibitors (MAOI) in double-blind controlled trials in this population. Moreover, evidence suggests that depressed patients who exhibit atypical features are more prone to relapse with SRIs than patients who do not have atypical features. MAOIs, on the other hand, have been shown to be effective, but are generally not well tolerated, and are associated with potentially severe drug and dietary interactions. Given this possible reduced response rate with some antidepressants in atypical depression, there is a need to find alternative treatments that are as effective as MAOIs, but better tolerated.

In addition, studies in humans and animals have suggested a link between brain histamine function and several other disorders relating to brain reward systems and internal regulatory control of behavior. These mechanisms are implicated in such aberrant human behaviors such as substance abuse and over-eating. Alcoholism is one of the world's most costly drug abuse problems and, with the exception of nicotine, is more costly to most countries than all other drug use problems combined. Overcoming alcoholism through behavioral modification based treatments alone is extremely difficult and has a high rate of recidivism.

Obesity is another disorder that has at least some basis in faulty regulatory mechanisms. Obesity adversely affects all body organs and bodily functions, especially the heart, blood vessels, joints and blood sugar metabolism. As a person's level of obesity increases, so does their risk for disease. It is estimated that up to 30 percent of all Americans are obese, and the economic cost in medical costs, reduced productivity and shortened life spans, as well as the toll on human dignity, is astronomical and probably realistically immeasurable. Certain subtypes of obesity may be particularly benefited by new approaches to treatment based on targeting internal regulatory mechanisms.

Hence, there is a continuing need for pharmaceutical approaches to complement behavioral approaches to the treatment of certain human disorders by targeting the underlying physiological mechanisms which may manifest as substance abuse or weight management difficulties.

SUMMARY OF THE INVENTION

Accordingly, the present invention provides methods for treating diseases that involve symptoms relating to these central histamine systems. Generally, these disorders are characterized by disturbances of mood, cognition, arousal, appetite regulation, and disorders characterized by addictive behaviors or dysregulation of the hypothalamic-pituitary-adrenal (HPA) axis that would benefit from a therapy that enhances histaminergic neurotransmission.

One embodiment of the invention is directed to methods for treating depression. Certain subtypes of depression, including, for example, atypical depression and the depressive aspect of bipolar disorder, are particularly amenable to treatment according to the present methods. The methods comprise administering an effective amount of an ($H_3$) receptor antagonist to an individual or patient in need thereof. An effective amount is an amount administered systemically, for example, orally, wherein the active crosses the blood brain barrier to impact central $H_3$ receptors to increase histaminergic neuroactivity.

Another embodiment of the invention is directed to methods for treating a patient suffering from, recovering from, or predisposed to, one or more disorders selected from binge eating disorder, narcolepsy, excessive daytime sleepiness, substance use disorders, and Prader Willi syndrome. The method comprises administration of an H3 antagonist to the patient.

According to another embodiment, methods are provided for treating patients suffering from disorders characterized at least in part by hypocortisolemia and decreased activity of the hypothalamic-pituitary-adrenal (HPA) axis. The methods comprise administration of an effective amount of an $H_3$ antagonist to the patient. A further embodiment is directed to methods for adjusting a circadian rhythm disturbance in an individual which comprises administration of an $H_3$ antagonist.

These and other embodiments of the invention will be understood more fully by reference to the Detailed Description, below.

DETAILED DESCRIPTION

Histamine is a neurotransmitter in the central nervous system that is involved in the regulation of sleep, appetite, cognition, and, perhaps, mood. Agents such as the first generation antihistamines that block histamine type 1 ($H_1$) receptors in the brain are known to cause sedation and increased appetite/weight gain. Betahistine, a drug approved in Canada and Europe for the treatment of vertigo associated with Meniere's disease is thought to produce its effects by increasing histamine levels, primarily by blocking presynaptic histamine type 3 ($H_3$) receptors, which causes increased release of histamine from the presynaptic neuron. In a study of vertigo in patients with multiple sclerosis, betahistine treatment also produced a statistically significant reduction in symptoms of fatigue.

MAO inhibitors have been shown to be superior to tricyclic antidepressants (TCAs) for the treatment of atypical depression. The effects of MAOI antidepressants on histamine suggest that drugs that increase histamine activity in the brain will have benefits in the treatment of depression. Furthermore, the relationship between the histamine system in the brain and HPA axis activity are such that a deficit in histamine function contributes to HPA hypoactivity. Therefore, treatments that increase CRH and HPA activity through enhanced histaminergic neurotransmission treat atypical depression by correcting hypoactivity of the HPA system that appears to be associated with this subtype of depression. Betahistine has been shown to increase HPA activity in rats. Hence, betahistine, administered in doses which yield an effective central concentration, should benefit patients with atypical depression, and other patients with other illnesses associated with clinically significant hypocortisolism, such as fibromyalgia, chronic fatigue syndrome, autoimmune disorders such as rheumatoid arthritis and multiple sclerosis, somatoform pain disorder and post-traumatic stress disorder.

Further, given the link between the brain histamine system and reward and pleasure centers in the brain, as well as the evidence for altered histamine function in patients with alcoholism, betahistine therapy as described in this claim would help reduce excessive alcohol consumption.

In placebo-controlled trials in patients with cerebrovascular dementia, betahistine has been shown to increase motor activity and improve cognitive functioning in patients with cerebrovascular dementia. Moreover, in animal studies, betahistine has been shown to decrease eating behavior. Another study in humans showed that a single dose of betahistine 64 mg had effects on arousal and vigilance that were greater than those observed with placebo, while a 32 mg dose of betahistine bad no effect. In light of this finding, and the relatively modest effect of betahistine on CNS functions in clinical studies using the standard doses of 32-48 mg/day, the present inventors determined that higher doses of betahistine (i.e. 64-300 mg) are more beneficial for the treatment indications disclosed herein.

Formulation and Bioavailability Considerations

Formulation considerations are important in medicinal applications employing betahistine. In particular, bioavailability and duration of action in the body associated with biologic half-life, must be taken into account. These features are important as the effect of betahistine in the brain specifically on histamine H3 receptors is both dose and duration dependent (Tighilet et al. 2005). Currently disclosed formulations are very poorly bio-available, that is, only a miniscule amount from an ingested oral tablet actually gets into the blood stream and subsequently to the brain. Solvay Pharmaceuticals, an original sponsor of betahistine for regulatory purposes, produced a formulation of betahistine dihydrochloride which was never characterized as to bioavailability. Typically in the pharmaceutical industry, a minimum bioavailability for the active pharmaceutical ingredient (API) is 30%.

An alternative formulation has been developed by Eicai (Tokyo, Japan), which is a betahistine mesylate. This product was recently analyzed by Chen et al. (Chen X. Y, Zhong D. F., Duan J. L., Yan B. X: LC-MS-MS analysis of 2-pyridylacetic acid, a major metabolite of betahistine: application to a phannacokinetic study in healthy volunteers. Xenobiotica. 2003 December; 33(12):1261-71) using modern methods and found to be less than 1% bioavailable. Almost the entire formulation is rapidly and exclusively metabolized in humans to 2-pyridylacetic acid, which has not been shown to have any biologic activity according to either the animal or human literature. Using a very sensitive and specific liquid chromatographic tandem mass spectrometric (LC-MS-MS), Chen et al. (2003) were able to detect trace amounts of two biologically active metabolites of betahistine, aminoethylbetahistine and hydroxyethylbetahistine. Although these metabolites do possess activity at histaminic receptors, their low concentrations after administration of the parent drug lead one to conclude that they are of no practical importance in the pharmacologic action of betahistine in humans.

An analysis of these facts leads to the surprising conclusion that 1) the predominant pharmacologic action of betahistine is solely due to the parent molecule, not active metabolites, and 2) current formulations are poorly suited for any delivery to the body and most specifically to the brain, due to i) extremely poor bioavailability and ii) extensive first-pass metabolism by the liver of betahistine. Furthermore, any formulation which delivers bioavailability of at least 10-40% for betahistine would be vastly superior to the current ineffective commercially available products which provide less than 1%. In addition, a new formulation which suppresses or retards first pass metabolism by the liver, would greatly improve bioavailability and would promote sufficient blood and brain concentrations of betahistine so as to promote a biological effect in the brain and impact histamine receptor H3 activity.

Bioavailability may be enhanced by mechanical dissolution enhancement by embedding the active ingredient, betahistine, in a matrix of suitable inert material to be ingested (ie wax, coated bead, lipid, or synthetic material). Bioavailability may also be enhanced by betahistine chemical modification or addition of molecules or substituents which block the active site for betahistine hydroxylation or which block the formation of 2-pyridylacetic acid. Bioavailability may be enhanced by the manufacture of a prodrug (e.g. lysine or similar molecule) whereby an ingredient is attached or linked to betahistine which allows betahistine to escape first-pass metabolism and which will enhance bioavailability. A prodrug is a pharmacologically inactive compound that is converted to the active form of the drug by endogenous enzymes or metabolism. It is generally designed to overcome problems associated with stability, toxicity, lack of specificity or limited (oral) bioavailability. Bioavailability may also be enhanced by a transdermal skin-patch like formulation which would bypass the first pass metabolism and achieve direct penetration into the blood and brain.

Biologic half-life of betahistine as determined by pharmacokinetic analysis (Chen et al., supra) is characterized by a high degree of variability (2-11 hours) with a mean of 5 hours. As a biologic effect in the brain is dependent upon the sustained availability of the active betahistine over a period of at least 6-12 hours it is crucial that an optimal formulation of betahistine exhibit a pharmacokinetic half-life ($t_{1/2}$) greater than 5 hours and preferably 8-12 hours. Once or twice daily dosing could thereby achieve a sustained effect of betahistine to block brain histamine H3 autoreceptors.

Mechanism of Action for Betahistine in Brain

Without wishing to be bound by theory, it is believed that the activity of betahistine at the H3 receptor autoreceptor promotes the release and synthesis of brain histamine. It is a blockade of H3 and antagonist properties at the H3 receptor, not betahistine's agonist properties at H1 receptors, that is believed central to betahistine's brain effects. This mechanism of action for betahistine is non-intuitive. The central brain effects, which are largely indirect, block the suppression of histamine synthesis and transmission by the H3 autoreceptor. Furthermore, the H3 antagonist properties of betahistine require higher doses, above 48 mg/day for biological effect in the brain.

Animal studies (Tighilet, B; Trottier, S; Lacour, M: Dose- and duration-dependent effects of betahistine dihydrochloride treatment on histamine turnover in the cat. Eur J Pharmacol. 2005 Oct. 31;523(1-3):54-63; Epub 2005 Oct. 14) using a betahistine dihydrochloride formulation at oral doses roughly equivalent to those currently given to humans for Meniere's Disease (ie 24-48 mg/day), as well as 2 fold, 5 fold and 10 fold higher doses, found that to achieve a rapid biological effect on histamine H3 autoreceptors, 5 fold and 10 fold higher equivalent doses were required.

This finding supports two critical aspects that are key to the present method of use: 1) substantially higher doses than those currently used for Meniere's Disease are required to achieve brain effects in histamine circuits via the action of betahistine on histamine H3 receptors; and 2) to achieve these higher brain concentrations of betahistine, 5-10 fold enhanced betahistine bioavailability to assure these brain concentrations is crucial. It is only at doses higher than 50 mg/day and, more preferably, above 96 mg/day, that the central brain action of the betahistine active on histamine H3 receptors is biologically relevant. This assertion is supported by Tighilet et al. which demonstrated in cats that orally administered betahistine at roughly the same dose used in humans currently (48 mg/day) produced no biologic effects on brain histamine or histamine H3 receptors. These findings lead to the surprising conclusion that doses higher than 48 mg/day, between 96 and 480 mg/day orally would be necessary to achieve a biologic effect in the brain via histamine H3 receptor activity promoted by betahistine.

Hence, an amount "effective" to treat disorders according to the present inventive methods comprises a dosage of at least about 48 mg per day. In more specific embodiment the effective amount comprises a dosage of between about 48 mg per day and about 480 mg per day, 48 and 300 mg per day, or between about 48 and 200 mg per day. In a very specific embodiment, the effective amount comprises a dosage of about 96 mg/day. Administration is preferably via systemic administration, including but not limited to oral administration.

Betahistine in Depression

Major depression is a serious, recurrent, and, not uncommonly, chronic disorder that affects millions of Americans. Although effective treatments are available, many patients do not respond, or do not reach full remission with currently available antidepressant medications. Moreover, medications that are available may cause side effects that limit their usefulness to a significant number of patients. For patients who suffer from major depression with atypical features (atypical depression), the agents that have been shown to be most effective (monoamine oxidase inhibitors or MAOIs) have a troublesome side effect profile and potentially serious drug/dietary interactions that reduce their benefit to this population.

One embodiment of the invention is directed to a method of treating depression comprising the step of administering an effective amount of an (H3) receptor antagonist to an individual in need thereof. In a specific embodiment, the $H_3$ receptor antagonist comprises betahistine or a pharmaceutically acceptable salts thereof, and in more specific embodiments the $H_3$ receptor antagonist comprises betahistine hydrochloride or betahistine mesylate. According to another specific embodiment, the $H_3$ receptor antagonist comprises at least one metabolite of betahistine or a pharmaceutically acceptable salt thereof.

Atypical depression, as defined in DSM-IV™ (American Psychiatric Association 2000), is a subtype of major depression characterized by mood reactivity and two or more of the following criteria: hypersomnia; increased appetite or weight gain; leaden paralysis; and longstanding sensitivity to interpersonal rejection. Studies estimate that between 16 and 23% of patients with unipolar depression present with atypical features, with even higher rates found in bipolar disorder in some studies.

According to specific embodiments of the inventive methods, the depression being treated comprises a subtype of depression and in a more specific embodiment the subtype comprises an atypical subtype of depression. According to further specific embodiments, "treating" comprises treating at least one symptom associated with the atypical subtype of depression. Exemplary symptoms include fatigue, hypersomnia and increased appetite/weight gain.

One potential advantage of using betahistine to treat patients with atypical depression is that it has an excellent tolerability profile. As noted, MAOIs, which are the current standard for treating atypical depression, are generally not well tolerated and are associated with potentially severe drug and dietary interactions. People who use MAOIs must adhere to numerous dietary restrictions and observe special precautions to avoid potentially serious complications. Furthermore, newer classes of antidepressant medications such as serotonin reuptake inhibitors (SSRIs), which are typically used first line to treat atypical depression, have not been shown to be as effective as MAOIs. Therefore, betahistine offers significant advantages over the most commonly prescribed antidepressant therapies with regard to effectively managing symptoms of depression both acutely and in the maintenance phase of treatment.

Bipolar Depression

Another subtype of depression that is benefited by treatment with betahistine is bipolar depression, which is the depressive state associated with bipolar disorder. Bipolar disorder has been linked higher rates of atypical features during the depressive phase. Conversely, patients with atypical depression have higher rates of first degree relatives with bipolar disorder than patients with depression without atypical features. As mentioned above, atypical depression appears to be linked to HPA axis activity and it is hypothesized that medications that increase cortisol levels may be therapeutic. Betahistine, in animal models, increases the cortisol response to certain types of stress (see above). In addition, lithium, which has been shown in placebo-controlled trials to be effective in treating bipolar depression, has intracellular effects that overlap with histamine's effects on second messenger systems. Specifically, both histamine (Donaldson J, Hill S J. Histamine-induced hydrolysis of polyphosphoinositides in guinea-pig ileum and brain. Eur J Pharmacol. 124:255-265, 1986) and lithium increase intracellular inositol monophosphate accumulation, which has been purported to be the mechanism underlying lithium's positive effects on mood. Moreover, when co-administered with lithium, histamine and histamine agonists directly enhance lithium's effects on the phosphatidylinositol second messenger system (Daum D R, Arias-Montano J A, Young J M. Histamine-induced inositol phosphate accumulation in HeLa cells: lithium sensitivity. Br J Pharmacol. 104:677-684, 1991). In addition, lithium treatment alters intracellular histamine levels in humans (Wood K, Harwood J, Coppen A. Platelet accumulation of histamine in controls, depressed and lithium-treated patients. J Affect Disord. 7:149-158, 1983).

Another property of $H_3$ antagonists relevant to the consideration of their use in bipolar disorder is their apparent anticonvulsant effects in animal models (Kakinoki H, Ishizawa K, Fukunaga M, Fujii Y, Kamei C. The effects of histamine $H_3$-receptor antagonists on amygdaloid kindled seizures in rats. Brain Res Bull. 46:461-465, 1998) As several antiepileptic agents have been shown to be effective treatments for bipolar disorder including the depressed phase of the illness (e.g., lamotrigine), the anticonvulsant properties of $H_3$ antagonists may facilitate any antidepressant effects that are seen. Moreover, as several anticonvulsant medications are effective in the prophylactic treatment of mania, $H_3$ antagonists such as betahistine may decrease the risk of switching into mania that is associated with antidepressant therapy. It is noteworthy that clozapine, an effective mood stabilizer, has significant $H_3$ antagonist effects (Rodrigues A A, Jansen F P, Leurs R, Timmerman H, Prell G D. Interaction of clozapine with the histamine $H_3$ receptor in rat brain. Br J Pharmacol. 114:1523-1524, 1995). Given the effects of histamine and $H_3$ antagonists on the phosphatidylinositol intracellular messenger system and the potential anticonvulsant effects of these compounds, it is a surprising conclusion that betahistine at higher doses would be effective for treating patients in the depressed phase of bipolar disorder.

Specifically, with regard to betahistine hydrochloride therapy for depression, treatment is initiated with 24-48 mg per day, and subsequently increased beyond this dose up to the range of 170-300 mg/day if needed. Alternatively, some patients may experience sustained benefit with a twice a day or three times per day dosing schedule. Fatigue, hypersomnia and increased appetite will respond more rapidly with betahistine therapy than with other traditional antidepressant treatments (i.e. 1-3 days as opposed to 2-3 weeks) whereas other symptoms of depression may take longer to respond. This increased rate of response for these symptoms is an advantage particularly for patients with atypical depression.

Furthermore, some patients will receive additional benefit with the use of betahistine or other $H_3$ antagonists in combination with traditional antidepressants such as SSRIs, particularly when there has been a partial response to initial therapy with a traditional antidepressant. The betahistine is preferably administered systemically and may be administered in any suitable form, including tablets, liquids, timed release capsules (i.e. oral sustained release formulations), sublingual dosing, transepidermal patches, subcutaneous sustained release devices, nasal sprays, rectal suppositories and injections.

Betahistine in Narcolepsy

Narcolepsy is a neurological disorder of sleep regulation that affects the control of sleep and wakefulness. Orexin (hypocretin) is deficient in narcoleptic patients, and plays a major role in the regulating and maintaining sleep/wakefulness states as well as energy homeostasis (Sakurai Sleep Medicine 2004). The four classic symptoms of narcolepsy are excessive daytime sleepiness, cataplexy, sleep paralysis and hypnagogic hallucinations. Histamine neurotransmission from the Tuberomamillary Nucleus (TMN) impacts this wake-active system and is thought to promote the waking state indirectly via the orexin 2 receptor (OX2R) located within the TMN. These effects of histamine on OX2R are mediated by histamine $H_3$ receptors as $H_3$ receptor antagonists have no effect to increase wakefulness in mice lacking the $H_3$ receptor (Toyota, H. et al. Behavioral characterization of mice lacking histamine $H_3$ receptors. Mol. Pharmacol. 62, 389-397 (2002).

A surprising consequence of these findings are that $H_3$ receptor antagonists such as betahistine should promote wakefulness and betahistine at doses higher than 48 mg/day and thereby acting as a $H_3$ receptor antagonist should be useful in sleep-related disorders, such as narcolepsy. For substantiation, it has recently come to light that modafinil (Provigil/Cephalon), a novel wakefulness-promoting drug for the treatment of narcolepsy, has been shown to increase hypothalamic histamine release (Ishizuka, T. et al. Modafinil increases histamine release in the anterior hypothalamus of rats. Neurosci. Lett. 339, 143-146 (2003).

Betahistine in Attention-deficit, Hyperactivity Disorder and Other Cognitive Impairments Histamine neurotransmission is pro-alerting while blockade of histamine $H_1$ receptors, or agonists at $H_3$ receptors produce sleep and produce a decline in cognitive functioning (e.g. the antihistamine diphenhydramine hydrochloride, Benadryl). $H_3$ receptor antagonists can improve cognitive performance in various animal models (Hancock, A. A. & Fox, G. B. in Milestones in Drug Therapy (ed. Buccafusco, S. J.). Birkhäuser, Basel, 2003). The effect of betahistine acting at doses higher than 48 mg/day and thereby as an H3 receptor antagonist is indirect through histamine circuit activity to enhance acetylcholine release in the prefrontal cortex and the hippocampus. The consequence is that betahistine should improve attention and working memory which are impaired in ADHD. In rats, a selective $H_3$ receptor antagonist, ABT-239, has demonstrated precognitive effects through enhancement of acetylcholine release in the prefrontal cortex and the hippocampus, improving learning in an inhibitory avoidance model of ADHD (Leurs et al. Nature Reviews Drug Discovery, 4:107-120, 2005).

Prader Willi Syndrome

Modulation of CNS histaminergic neurotransmission represents novel and surprising mechanism to reduce satiety and therefore reduce caloric consumption and control body weight. Though the role of neuronal histamine in food intake has been established for many years, and the blockade of its action at hypothalamic $H_1$ receptors has been indicated as the mechanistic action of weight gain after therapy with various antipsychotics (e.g. olanzapine), these actions are separate from actions on the $H_3$ histamine receptor which impact the anorectic actions of known mediators of the feeding cycle (e.g. leptin, amylin and bombesin) (Hancock, A. A. $H_3$ Receptor antagonists/inverse agonists as anti-obesity agents. Curr. Opin. Investig. Drugs 4, 1190-1197 (2003).

Brain specific $H_3$ receptors are implicated in the regulation of histamine release in the hypothalanus, an area rich in regulation circuitry for feeding hormones ghrelin and leptin. Evidence from $H_3$ receptor antagonists suggest that their anti-obesity efficacy, including reduction in food intake is associated with a lowering of circulating leptin and ghrelin levels. It is surprising that betahistine, at doses greater than 48 mg/day, and therefore acting as an $H_3$ antagonist, would have an indirect effect on satiety and eating behavior in Prader-Willi Syndrome, an orphan disease resulting in a decrease in food craving and food consumption, meal size, and behavioral interventions required to reduce same.

Prader-Willi Syndrome (PWS) is an "orphan disease" with a prevalence of 1/50,000 and results from the absence of expression of the paternal copy of as yet unidentified maternally imprinted gene(s) at the genetic locus 15(q11-13). This syndrome is associated with hyperphagia, leading to morbid obesity if the food environment is unsupervised. The eating behavior has been characterized as a constant desire to eat, which, together with reduced physical activity in those with PWS, and energy requirements that are 50-75% of the normal, means access to food must be strictly controlled to prevent extreme obesity.

It has recently been discovered that PWS have normal neural representations of hunger but do not experience fullness or satiety, even when high caloric food is consumed. It has been hypothesized that PWS patients lack this sense of fullness because they are insensitive to the hormone ghrelin, with fasting ghrelin levels 4 fold higher than equally obese individuals without PWS. Ghrelin is produced by P/D1 cells lining the fundus of the human stomach and has been discovered to stimulate appetite. Ghrelin levels typically increase just prior to meals and decrease after meals. Ghrelin is thought of as the counterpart to leptin, which is produced by adipose tissue and induces satiation. Ghrelin has also been found to stimulate secretion of growth hormone from the anterior pituitary gland.

Alcohol and Other Substance Use Disorders

Studies in both humans and animals have drawn a link between brain histamine function and alcohol consumption. One study showed that $H_3$ antagonists reduce alcohol consumption in alcohol-preferring rats (Lintunen et al., 2001). In humans, a polymorphism in the gene for histamine n-methyl transferase (HNMT), the major metabolizing enzyme for histamine, was reported to be more common in alcoholics than in healthy control subjects (Oroszi et al., 2005). This suggests that lower brain histamine levels may be a predisposing factor for excessive alcohol consumption. What is not obvious is that betahistine treatment at a higher dose than that used in Meniere's disease would produce an increase in central histamine levels through antagonism of the $H_3$ receptor that may decrease cravings for alcohol in patients with alcohol use disorders.

In addition, evidence suggests that histamine is involved in the mechanisms of action of several other drugs of abuse, including opioids, psychostimulants such as cocaine and methamphetamine, and nicotine. Specifically, one study reported increased methamphetamine-induced locomotor hyperactivity and facilitation of behavioral sensitization in animals with depleted CNS histamine levels suggesting that histamine may inhibit the development of these behavioral markers of drug dependence (Iwabuchi, K. et al., (2004) "Methamphetamine and brain histamine: a study using histamine-related gene knockout mice," Ann NY Acad Sci 1025: 129-134). Moreover, histamine agonists and the histamine precursor 1-histidine have been reported to block these phenomena, and in addition, inhibit stereotypical behaviors produced by methamphetamine (see Itoh, Y. et al. (1984) "Neuronal histamine inhibits methamphetamine-induced locomotor hyperactivity in mice," Neurosci Lett 48(3): 305-9; Masukawa, K. et al., (1993) "Differential modification of the rewarding effects of methamphetamines and cocaine by opioids and antihistamines," Psychopharmacology (Berl) 111(2): 139-43; Ito, C. K. et al. "Effects of histamine agents on methamphetamine-induced stereotyped behavior and behavioral sensitization in rats," Psychopharmacology (Berl) (1997) 130(4):362-7) and cocaine (Masukawa, supra). Moreover, treatment with medications that block the H1 receptor have been shown to enhance the ability of animals to detect the rewarding effects of cocaine, suggesting that enhancing neuronal histamine would have the opposite effect. Antihistamines have also been shown to enhance the rewarding effects of opioid drugs (Kamei, J. K., et al. (2003) "Effects of second generation of histamine H1 antagonists, cetirizine and ebastine, on the antitussive and rewarding effects of dihydrocodeine in mice," Psychopharmacology (Berl) 166(2): 176-80). Finally, stimulation of central nicotinic receptors has been shown to inhibit histaminergic activity in the brain. All of these studies suggest that enhancement of central histaminergic tone via blockade of $H_3$ receptors with betahistine would likely benefit patients with one or more of these substance dependence disorders.

Binge Eating Disorder (BED)

Changes in eating behavior in animal studies with betahistine and other $H_3$ antagonists suggest that it may be beneficial to patients with pathologically increased appetite. For example, betahistine has been shown to decrease eating behavior in rats in a dose-dependent manner (Szelag A, Trocha M, Merwid-Lad A. Betahistine inhibits food intake in rats. Pol J Pharmacol. 53:701-707, 2001). In studies of humans with disorders associated with binge eating, altered activity of centrally-acting hormones that regulate satiety and appetite such as leptin, neuropeptide Y (NPY), and peptide YY has been reported (Monteleone P, et al. Ghrelin and leptin responses to food ingestion in bulimia nervosa: implications for binge-eating and compensatory behaviours. Psychol Med. 33:1387-94 (2003), and Monteleone P, Di Lieto A, Tortorella A, Longobardi N, Maj M. Circulating leptin in patients with anorexia nervosa, bulimia nervosa or binge-eating disorder: relationship to body weight, eating patterns, psychopathology and endocrine changes. Psychiatry Res. 94:121-9, 2000). Histamine actions in the hypothalamus have been linked to the actions of several of these hormones. Specifically, leptin administration in animals has been shown to increase histamine activity (Itateyama E, Chiba S, Sakata T, Yoshimatsu H. Hypothalamic neuronal histamine in genetically obese animals: its implication of leptin action in the brain. Exp Biol Med 228:1132-7, 2003). In addition, $H_3$ antagonists have been shown to decrease the orexigenic effects of NPY in rats (Ito E, Fujimiya M, Inui A. Thioperamide, a histamine $H_3$ receptor antagonist, suppresses NPY-but not dynorphin A-induced feeding in rats. Neuroendocrinology; 82:70-7, 2005), and to suppress the effects of peptide YY on feeding behavior (Ito E, Fujimiya M, Inui A. Thioperamide, a histamine $H_3$ receptor antagonist, powerfully suppresses peptide YY-induced food intake in rats. Biol Psychiatry. 45:475-81, 1999). It is surprising that betahistine in higher doses would increase hypothalamic histamine activity and thereby produce an appetite suppressing effect that would be beneficial in BED and other disorders associated with bingeing behaviors.

One embodiment of the invention is directed to methods for treating a patient suffering from, recovering from, or predisposed to, one or more disorders selected from binge eating disorder, narcolepsy, excessive daytime sleepiness, substance use disorders, and Prader Willi syndrome. The method comprises administration of an $H_3$ antagonist to the patient suffering from recovering from, or predisposed to, the particular disorder being treated. In a specific embodiment the substance abuse disorder comprises alcohol abuse. The $H_3$ antagonist comprises betahistine or any pharmaceutically acceptable salt thereof PTSD and Hypocortisolemic Disorders A number of psychiatric and medical disorders have been associated with low cortisol and/or decreased activity of the HPA axis. Patients who demonstrate severe anxiety due to post-traumatic stress disorder (PTSD) have been shown to exhibit low basal cortisol levels as well as enhanced negative feedback of the HPA axis. Moreover, a recent study demonstrated that giving exogenous corticosteroids can diminish certain types of phobic anxiety, suggesting that low basal cortisol levels or a sluggish cortisol response to stress may contribute to pathological anxiety (Soravia L M, Heinrichs M, Aerni A, Maroni C, Schelling G, Ehlert U, Roozendaal B, de Quervain D J. Glucocorticoids reduce phobic fear in humans. Proc Natl Acad Sci USA. 103:5585-90, 2006). As mentioned previously, histamine and $H_3$ antagonists such as betahistine have been shown to enhance the secretion of ACTH and cortisol through a mechanism that may include decreasing negative feedback of the HPA axis. This property appears to be shared with the MAOI antidepressants, which also are also effective in PTSD.

Other disorders that have been characterized by low HPA axis activity include fibromyalgia, chronic fatigue syndrome (CFS), autoimmune disorders such as rheumatoid arthritis and multiple sclerosis, and somatoform pain disorder. As in PTSD, patients with CFS have been reported to exhibit low basal cortisol and enhanced feedback of the axis as demonstrated by increased suppression of cortisol secretion with dexamethasone (Gaab J et al. Low-dose dexamethasone suppression test in chronic fatigue syndrome and health. Psychosom Med. 64:311-8, 2002). Studies using dynamic tests of the HPA axis in patients with fibromyalgia also suggest a relative adrenal hyporesponsivenss to activation of the axis (Griep et al. Altered reactivity of the hypothalamic-pituitary-adrenal axis in the primary fibromyalgia syndrome. J Rheumatol. 20:469-74, 1993). It is surprising that betahistine, at doses greater than 48 mg/day, and therefore acting as a central $H_3$ antagonist, would have an indirect stimulating effect on HPA axis function in patients with these disorders characterized by diminished HPA axis activity. Moreover, as fatigue is a common complaint in patients with these disorders, it is likely that the direct alertness-promoting effects of increasing hypothalamic histamine release with this higher dose of betahistine would be beneficial to these patients as well.

Hence, according to another embodiment of the invention, methods are provided for treating patients suffering from disorders characterized at least in part by hypocortisolemia and decreased activity of the hypothalamic-pituitary-adrenal (HPA) axis. The methods comprise administration of an effective amount of an $H_3$ antagonist to the patient. Non-limiting examples of these disorders which may be effectively treated by the inventive method include, but are not limited to, post traumatic stress disorder, fibromyalgia, chronic fatigue syndrome, somatoform pain disorder, and auto-immune disorders such as multiple sclerosis and rheumatoid arthritis. The $H_3$ antagonist comprises betahistine or any pharmaceutically acceptable salt thereof.

Circadian Rhythm-Based Disorders

Histamine has been implicated in the diurnal regulation of sleep/arousal, appetite, and other biological rhythms, such as diurnal variation in cortisol levels (see Itowi N., Yamatodani A., Cacabelos R., Goto M., Wada H. 1989. Effect of histamine depletion on circadian variations of corticotropin and corticosterone in rats. *Neuroendocrinology* 50(2):187-92). Specifically, histamine has been shown to produce shifts in circadian rhythms that are similar to those produced by light (see Cote N. K, Harrington Me. Histamine phase shifts circadian clock in a manner similar to light. *Brain Res* 1993;613:49-51). Patients with seasonal affective disorder have been hypothesized to suffer from disturbances in circadian rhythms and often benefit from light treatment. Moreover, patients with seasonal affective disorder have been shown to be more likely to exhibit reverse vegetative symptoms such as hypersomnia and hyperphagia, which may benefit from treatments that increase brain histamine levels, including treatments comprising administration of $H_3$ antagonists such as betahistine in amounts or administration routes calculated for efficacy in the CNS.

Another embodiment of the invention is directed to methods of adjusting a circadian rhythm disturbance in an individual. The methods comprise administration of an $H_3$ antagonist. A non-limiting example of a disorder underpinned by a circadian rhythm disturbance is seasonal affective disorder (SAD). Although SAD is defined by the pattern of depressive episodes in DSM-IV, the atypical depressive symptoms of hypersomnia, hyperphagia, and weight gain are all more frequently found in SAD patients compared to matched non-seasonal patients. Interestingly, SAD patients are more likely to have alcoholism in their families.

EXAMPLES

The following examples illustrate specific embodiments of the present invention and are not intended to limit the scope thereof as set forth in the claims.

Example 1

This example illustrates use of betahistine in treatment of depression, and, in particular, treatment of atypical depression.

Dosing begins with 48 mg per day, and subsequently increases up to the range of 150-300 mg/day if needed. Alternatively, some patients may experience sustained benefit with a twice a day or three times per day dosing schedule. The rationale for the effectiveness of this dosing schedule, which is considerably higher than that used for treatment of Meniere's disease, is based on two key points. First, evidence from animal studies show that betahistine concentrations in the CNS after peripheral administration of the drug are approximately half the levels achieved in the plasma with a particular dose (Guth, P. S. (2001) "The pharmacology of betahistine in the context of the vestibular system," *Acta Otorhinolaryngol Ital*, 21 (3 Suppl 66): 16-23). This suggests that higher doses are needed to produce direct CNS effects. Moreover, Tighilet et al. (2005) demonstrated that doses in cats that were able to produce a rapid effect on $H_3$ autoreceptors were equivalent to doses in humans that were 5-10 fold higher than the dose that is shown to be effective for Meniere's Disease (i.e. up to 48 mg/day).

In fact, the dose range commonly used in Meniere's disease may be too low to produce broader CNS effects such as improvement in mood, vigilance and suppression of excessive eating. At a dose of 32 mg/day, betahistine produces no noticeable CNS-stimulating effects compared to placebo in healthy volunteers as measured by neuropsychological testing and EEG recordings, and at 64 mg/day it has only mild stimulant-like effects (Vermeeren, A. and O'Hanlon, J. F. (1995) "A 4-way, double blind, placebo and active drug controlled study for determining whether betahistine in single 32 and 64 mg doses enhances vigilance and electrocortical arousal in man" Study Report H 108.922 NS-IHP 95.55. Maastricht, The Netherlands, Institute for Human Psychopharmacology: 1-17. This 64 mg dose is higher than the maximum dose of 48 mg approved for the treatment of vertigo, which may explain why stimulant effects and other direct CNS effects are generally not reported by patients receiving betahistine in studies evaluating its effectiveness for the treatment of Meniere's disease (Vermeeren and O'Hanlon, supra). Second, it has been suggested that in Meniere's disease betahistine may produce its effect primarily through a peripheral mechanism in the inner ear, as opposed to direct central nervous system effects (Guth, supra, and Lacour, M. and Sterkers, O. (2001) "Histamine and betahistine in the treatment of vertigo elucidation of mechanisms of action" *CNS Drugs*, 15: 853-70).

As betahistine is extremely well tolerated, with no toxic effects having been reported in medically healthy individuals, it appears to be safe to administer higher doses that may produce the desired CNS effects, such as the stimulant-like effects and positive effects on mood, that would be beneficial to patients with major depression with atypical features and other diseases that would benefit from enhancing CNS histaminergic neurotransmission.

Many patients will receive benefit with once daily dosing with betahistine particularly when using a sustained-release form of the drug. Alternatively, when using an immediate release form of the drug, based on its relatively short half-life, some patients will experience sustained benefit with a twice a day or three times per day dosing schedule, particularly for the effects on the symptoms of hypersomnia, fatigue, and appetite. Fatigue, hypersomnia and increased appetite will respond more rapidly with betahistine therapy than with other traditional antidepressant treatments (i.e. 1-3 days) whereas other symptoms of depression will respond in the time-frame usually seen with traditional antidepressants (2-6 weeks). This increased rate of response for these symptoms will be an advantage particularly for patients with atypical depression, or other diseases characterized by fatigue, excessive somnolence, cognitive deficits, or hyperphagia. Furthermore, some patients will receive additional benefit with the use of betahistine or other $H_3$ antagonists in combination with traditional antidepressants such as SSRIs, SNRIs, or atypical antidepressants such as bupropion, mirtazapine or nefazodone, particularly when there has been a partial response to initial therapy with the traditional antidepressant.

The betahistine may be administered in any suitable form, including tablets, liquids, timed release capsules (i.e. oral sustained release formulations), sublingual dosing, transepidermal patches, subcutaneous sustained release devices, nasal sprays, rectal suppositories and injections. Sustained-release formulations would be the preferred method of administration of betahistine for any disorder of the CNS that may benefit from enhancement of CNS histaminergic activity. The advantages of a sustained-relief formulation include the potential for using lower doses of the drug while still maintaining adequate CNS penetration, and thereby minimizing certain peak-related peripheral side effects that may occur with $H_3$ receptor blockade. Betahistine could also be administered in the form of a pro-drug that would increase bioavailability or improve blood-brain-barrier penetration of the drug, thereby allowing lower doses of the drug to be used and minimizing side effects due to peripheral mechanisms.

Example 2

This example illustrates a method of treating Binge Eating Disorder (BED) (see http://www.ahrq.gov/downloads/pub/evidence/pdf/eatingdisorders/eatdis.pdf) using betahistine hydrochloride.

Treatment may be initiated with 48 mg per day in a formulation achieving a minimum sustained concentration in plasma of 200 ng/ml for a minimal period of 4-6 hours. Depending upon intensity and duration of suppression of both appetite and binge episodes in a patient suffering from BED, dose can subsequently be increased up to a range of 96-300 mg/day if needed, to produce a reduction in BED specific associated symptoms. This higher subsequent dose range (96-300 mg/day) is necessary to provide higher sustained plasma concentrations (ie. greater than 400 ng/ml) so as to cross the blood-brain barrier in sufficient concentration for betahistine and its primary metabolite, 2-pyridylacetic acid, to produce specific brain activation in the hypothalamus and other brain centers to reduce craving, enhance satiety, and dampen habit pathway circuits in the brain leading to binging.

As BED is a chronic and continuous disorder, it is preferable to provide sustained betahistine hydrochloride therapy which is consistent with a long-acting, sustained-release, or once-daily administration of betahistine hydrochloride. Alternatively, some patients will experience sustained benefit with a twice a day or three times per day dosing schedule. Binging, food craving, and other associated BED symptoms will respond more rapidly with betahistine therapy than with other treatments (i.e. 1-3 days) whereas treatment of BED with fluoxetine takes 3-4 weeks for response (see William P. Carter, James I. Hudson, Justine K. Lalonde, Lindsay Pindyck, Susan L. McElroy Harrison G. Pope Jr. Pharmacologic treatment of binge eating disorder; International Journal of Eating Disorders, 34 Suppl:S74-88, 2003). The rationale for this rapid and more immediate reduction in BED symptoms is believed to be associated with the pre-synaptic antagonism on the histamine $H_3$ receptors which directly regulate histamine production and quantity of histamine release within the brain and the hypothalamus in particular (see Malmlof, K., et al. "Influence of a selective histamine H3 receptor antagonist on hypothalamic neural activity, food intake and body weight," *Int J Obes* (Lond) 2005 December; 29(12):1402-12, and Hancock A A. "The challenge of drug discovery of a GPCR target: analysis of preclinical pharmacology of H3 antagonists/inverse agonists," *Biochemical Pharmacology* 71:1103-1113, 2006). This rapid onset of action which is unique to betahistine hydrochloride therapy is also associated with decreased food craving, appetite, and food consumption which have been intractable to fluoxetine (currently labeled for BED by the Food and Drug Administration).

Rapid treatment onset and broader range of BED symptom reduction with betahistine hydrochloride is advantageous for patients with BED. The betahistine may be administered in any suitable form, including tablets, liquids, fast-melt tablets, sublingual dosing, transepidermal patches, subcutaneous sustained release devices, nasal sprays, rectal suppositories and injections. As the preferred method of use requires sustained plasma concentrations over a minimum of 4-6 hours with a preference toward even longer availability of 6-12 hours, a timed release tablet or capsule (i.e. oral sustained release formulations) would seem ideally suited. Specifically such a sustained controlled release could be achieved by a particular formulation of cross-linked amylose carrier. Alternatively the attachment of a chemically inert carrier molecule to betahistine would allow for the formulation of a pro-drug, which upon exposure to the environment of the stomach or intestine would slowly and consistently release betahistine for absorption.

Example 3

The following example illustrates the use of betahistine to treat Prader-Willi Syndrome (PWS). As noted above, PWS is a genetic disorder which results from the absence of expression of the paternal copy of as yet unidentified maternally imprinted gene(s) at the genetic locus 15(q11-13). A recent epidemiological study estimates an incidence of, 1 in 25 000 births, and a population prevalence of, 1 in 50 000 making it an orphan disease. In a patient with PWS there is a rapid onset of hyperphagia and obesity between the ages of 1-6 years, which is sustained into adulthood. Without adequate dietary control, the extreme hyperphagia in PWS leads to obesity-related morbidity, such as cardiopulmonary disease, type 2 diabetes mellitus, thrombophlebitis, chronic leg edema and mortality at 35 years. The abnormal feeding behavior includes a morbid obsession with food, food stealing, stealing money to buy food, hording and foraging, pica behavior, reduced satiety, and earlier return of hunger after eating. Research suggests that pharmacological treatment with anorexigenic agents that act through central monoamine and 5-hydroxytryptamine (5-HT) pathway, are not beneficial in treating hyperphagia and obesity associated with PWS.

The eating behaviour of PWS has been characterized as a constant desire to eat, which, together with reduced physical activity in those with PWS, and energy requirements that are 50-75% of the normal, means access to food must be strictly controlled to prevent extreme obesity. PWS patients do not respond to the normal satiety signals of food after a meal and tend to consume more food for longer. It has been discovered that PWS patients continue to eat longer and eat on average three times more calories (PWS 1292 vs control 369 kcal) than controls. This significantly greater amount of food appears to be required in those with PWS to bring about a similar change in feelings of hunger, as measured by visual analogue scales, in comparison to normal subjects.

Furthermore, it has been demonstrated that feelings of hunger in PWS are correlated with the extent of change in blood glucose levels, which, in PWS reaches above the accepted physiological range. Lindgren et al. (Lindgren A C, Barkeling B, Hagg A, Ritzen E M, Marcus C, Rossner S. Eating behavior in Prader-Willi syndrome, normal weight, and obese control groups. J Pediatr 2000; 137: 50-55) found that those with PWS showed nondecelerating eating curves, a slower eating rate and a longer duration of eating compared to both lean and obese children without PWS. Together, these findings suggest that those with PWS have decreased satiation as opposed to extreme hunger, and that the satiety response in those with PWS is at least delayed, if not insensitive, to food.

This lack of satiety has a hypothalamic basis, which demonstrated by functional neuroimaging in individuals with PWS. Shapira et al. (Shapira N A, Lessig M C, He A G, James G A, Driscoll D J, Liu Y. Satiety dysfunction in Prader-Willi syndrome demonstrated by fMRI. J Neurol Neurosurg Psychiatry 2005; 76: 260-262) showed a significant delay in the negative response of the hypothalamus to glucose ingestion in those with PWS, in comparison to obese and normal-weight groups. It was demonstrated that the neural representation of hunger and associated experience is similar in PWS to those without the syndrome. From PET imaging and behavioral data, it appears that there is a dysfunction in the satiety system demonstrated when comparing the neural activity following meals of different energy values. PWS can detect a change in their internal states, which they interpret as increasing fullness but require a higher-energy meal to produce activation of the medial and lateral orbital frontal cortex corresponding to an experience of fullness. The rationale for using betahistine for PWS stems from the presence, though weak, of satiety signaling in the disease which may be selectively and quantitatively enhanced through the use of betahistine to promote histamine receptor H3 antagonism in the brain and thereby treat PWS specific symptoms (see Malmlof, K et al. "Influence of a selective histamine H3 receptor antagonist on hypothalamic neural activity, food intake and body weight" Int J Obes (Lond). 2005 December; 29(12):1402-12).

Specifically, with regard to betahistine hydrochloride therapy for PWS, treatment may be initiated with 48 mg per day in a formulation designed to achieve a minimum sustained concentration in plasma of 200 ng/ml for a minimal period of 4-6 hours. To augment and magnify the body's own signals for satiety, higher doses of betahistine may subsequently be achieved up to a range of 96-300 mg/day if needed, to produce a reduction in PWS specific associated symptoms. This higher subsequent dose range (96-300 mg/day) is necessary to provide higher sustained plasma concentrations (ie. greater than 400 ng/ml) so as to cross the blood-brain barrier in sufficient concentration for betahistine and its primary metabolite, 2-pyridylacetic acid, to produce specific brain activation in the hypothalamus and other brain centers to reduce abnormal feeding behavior, decrease obsession with food, hording and foraging, pica behavior, reduce overall food intake at meals, and forestall the return of hunger, enhance satiety, and dampen habit pathway circuits in the brain leading to PWS behavior. As PWS is a chronic and continuous disorder, it is preferable to provide sustained betahistine hydrochloride therapy which is consistent with a long-acting, sustained-release, or once-daily administration of betahistine hydrochloride.

Alternatively, some patients will experience sustained benefit with a twice a day or three times per day dosing schedule. Abnormal feeding behavior, obsessions with food, hording and foraging, pica behavior, and abnormal meal size and patterning will respond to betahistine therapy because it impacts directly the feeding and satiety signaling pathways in the brain. These satiety signaling pathways are selectively activated by histamine $H_3$ antagonists such as betahistine. The betahistine may be administered in any suitable form, including tablets, liquids, fast-melt tablets, sublingual dosing, transepidermal patches, subcutaneous sustained release devices, nasal sprays, rectal suppositories and injections. As the preferred method of use requires sustained plasma concentrations over a minimum of 4-6 hours with a preference toward even longer availability of 6-12 hours, a timed release tablet or capsule (i.e. oral sustained release formulations) would seem ideally suited. Specifically such a sustained controlled release could be achieved by a particular formulation of cross-linked amylose carrier. Alternatively the attachment of a chemically inert carrier molecule to betahistine would allow for the formulation of a pro-drug, which upon exposure to the stomach or intestine environment would slowly and consistently release betahistine for absorption.

Example 4

The following example illustrates treatment of alcohol abuse or dependence and other substance use disorders using formulations of betahistine.

Treatment of a patient suffering from alcohol abuse is initiated with a dose 50 mg per day, betahistine hydrochloride, increasing to the range of 100-300 mg/day if needed. For many patients a dose of 200 mg will produce the substantial reduction in the craving for alcohol. Moreover, many patients will notice a beneficial decreased tolerance for alcohol that will greatly reduce the amount of alcohol consumed when they drink, similar to what has been reported with histamine treatment of schizophrenic patients with alcohol use problems.

The rationale for the effectiveness of this dosing schedule is based in part on the observation that higher (greater than about 48 mg/day) doses of betahistine will be required to produce the direct CNS effects required to reduce the craving and tolerance for alcohol. Most patients will receive benefit with once daily dosing with betahistine particularly when using a sustained-release form of the drug. Alternatively, when using an immediate release form of the drug, based on its relatively short half-life, some patients may experience sustained benefit with a twice a day or three times per day dosing schedule. Cravings for alcohol will respond in a timeframe of 2-6 weeks, although some patients may notice rapid effects once the dose is titrated to 150-200 mg. Furthermore, some patients may receive additional benefit with the use of betahistine or another $H_3$ antagonist in combination with traditional pharmacotherapy for alcohol dependence such as naltrexone, (oral or extended-release injection), or acamprosate, particularly when there has been a partial response to initial therapy with the traditional anti-craving medication.

Betahistine may be administered in any suitable form, including tablets, liquids, timed release capsules (i.e. oral sustained release formulations), sublingual dosing, transepidermal patches, subcutaneous sustained release devices, nasal sprays, rectal suppositories and injections. Sustained-release formulations are a highly desirable method of administration of betahistine for any disorder of the CNS that may benefit from enhancement of CNS histaminergic activity. The advantages of a sustained-relief formulation include the potential for using lower doses of the drug while still maintaining adequate CNS penetration, and thereby minimizing certain peak-related peripheral side effects that may occur with $H_3$ receptor blockade. Betahistine may also be administered in the form of a pro-drug that would increase bioavailability or improve blood-brain-barrier penetration of the drug, thereby allowing lower doses of the drug to be used and minimizing side effects due to peripheral mechanisms.

While certain embodiments of the present invention have been discussed in detail and exemplified above, the scope of the invention should not be construed as limited thereby, but should be interpreted as defined by the claims.

What is claimed:

1. A method of treating depression comprising the step of administering an effective amount of an $H_3$ receptor antagonist to an individual in need thereof, wherein the $H_3$ receptor antagonist is selected from the group consisting of betahistine and a pharmaceutically acceptable salt of betahistine.

2. The method according to claim 1, wherein the pharmaceutically acceptable salt of betahistine comprises betahistine hydrochloride or betahistine mesylate.

3. A method according to claim 1, wherein depression comprises an atypical subtype of depression.

4. The method according to claim 3, wherein said treating comprises treating at least one symptom associated with the atypical subtype of depression, wherein the at least one symptom is selected from the group consisting of fatigue, hypersomnia and increased appetite/weight gain.

5. The method according to claim 1 wherein the depression comprises bipolar depression.

6. The method according to claim 1, wherein an effective amount comprises a dosage of at least about 48 mg per day.

7. The method according to claim 6, wherein the dosage is administered orally.

8. The method according to claim 7 wherein the effective amount comprises a dosage of between about 48 mg per day and about 480 mg per day.

9. The method according to claim 8 wherein the effective amount comprises a dosage of about 96 mg/day.

* * * * *